United States Patent
Ni

(10) Patent No.: US 11,918,548 B2
(45) Date of Patent: Mar. 5, 2024

(54) TREATMENT OF AVASCULAR OR HYPOVASCULAR MICRO-TUMORS

(71) Applicant: Katholieke Universiteit Leuven, Leuven (BE)

(72) Inventor: Yicheng Ni, Herent (BE)

(73) Assignee: Katholieke Universiteit Leuven, Leuven (BE)

( * ) Notice: Subject to any disclaimer, the term of this patent is extended or adjusted under 35 U.S.C. 154(b) by 180 days.

(21) Appl. No.: 16/628,904

(22) PCT Filed: Jul. 4, 2018

(86) PCT No.: PCT/EP2018/068141
§ 371 (c)(1),
(2) Date: Jan. 6, 2020

(87) PCT Pub. No.: WO2019/008064
PCT Pub. Date: Jan. 10, 2019

(65) Prior Publication Data
US 2020/0138739 A1 May 7, 2020

(30) Foreign Application Priority Data

Jul. 7, 2017 (GB) .................................... 1710936
Aug. 7, 2017 (LU) .................................... 100362

(51) Int. Cl.
| | | |
|---|---|---|
| *A61K 31/09* | (2006.01) | |
| *A61K 9/00* | (2006.01) | |
| *A61K 31/122* | (2006.01) | |
| *A61K 31/42* | (2006.01) | |
| *A61K 31/661* | (2006.01) | |

(Continued)

(52) U.S. Cl.
CPC ............ *A61K 31/09* (2013.01); *A61K 9/0019* (2013.01); *A61K 31/42* (2013.01); *A61K 31/661* (2013.01); *A61P 35/00* (2018.01); *A61K 31/122* (2013.01); *A61K 33/18* (2013.01)

(58) Field of Classification Search
CPC .... A61K 2300/00; A61K 31/09; A61K 31/34; A61K 31/343; A61K 31/4184; A61K 31/44; A61K 31/661; A61K 31/122; A61K 31/42; A61K 9/0019; A61K 33/18; A61P 35/00
See application file for complete search history.

(56) References Cited

U.S. PATENT DOCUMENTS

| | | |
|---|---|---|
| 9,353,038 B2 | 5/2016 | Huang et al. |
| 2007/0178107 A1 | 8/2007 | Awdalla |
| 2008/0214509 A1 | 9/2008 | Kerbel et al. |

(Continued)

FOREIGN PATENT DOCUMENTS

| | | |
|---|---|---|
| CN | 101073561 | 11/2007 |
| WO | WO 2019/008064 | 1/2019 |

OTHER PUBLICATIONS

Huaijun et al., Investigative Radiology: Jan. 2009—vol. 44—Issue 1—p. 44-53. (Year: 2009).*

(Continued)

*Primary Examiner* — Jean P Cornet
(74) *Attorney, Agent, or Firm* — Fish & Richardson P.C.

(57) ABSTRACT

The invention relates to vascular disrupting agent (VDA) such as combretastatins for treating avascular or hypovascular micro-tumors with a diameter below 20 mm.

9 Claims, 7 Drawing Sheets

Figure 1:
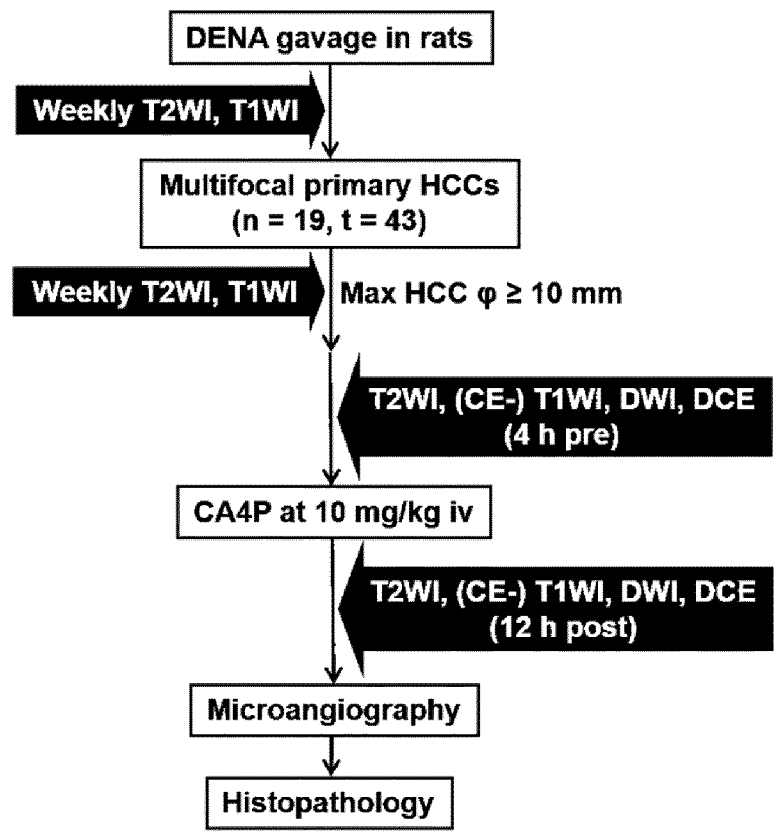

(51) Int. Cl.
A61K 33/18 (2006.01)
A61P 35/00 (2006.01)

(56) References Cited

U.S. PATENT DOCUMENTS

2008/0261982 A1 10/2008 Ruey-Min et al.
2010/0168036 A1 7/2010 Gill et al.
2011/0038795 A1* 2/2011 Ni .................... A61P 43/00
424/1.85

OTHER PUBLICATIONS https://blogs.kent.ac.uk/jonw/files/2015/01/PharmacologyRevisedClean.pdf to Kent 2015. (Year: 2015).*
Sica, American Journal of Roentgenology, vol. 174, Issue 3, Mar. 2000 (Year: 2000).*
Bilenker et al., "Phase I trial of combretastatin a-4 phosphate with carboplatin," Clin Cancer Res., Feb. 2005, 11(4):1527-1533.
Buijs et al., "Quantitative proton MR spectroscopy as a biomarker of tumor necrosis in the rabbit VX2 liver tumor," J Vasc Interv Radiol., Aug. 2011, 22(8):1175-1180.
Chen et al., "Diffusion weighted imaging in small rodents using clinical MRI scanners," Methods., Sep. 2007, 43(1):12-20.
Chen et al., "Enhanced antitumor efficacy of a vascular disrupting agent combined with an antiangiogenic in a rat liver tumor model evaluated by multiparametric MRI," PLOS One, Jul. 2012, 7(7):e41140, 1-12.
Cooney et al., "Drug insight: vascular disrupting agents and angiogenesis—novel approaches for drug delivery," Nat Clin Pract Oncol., Dec. 2006, 3(12):682-692.
Delmonte et al., "AVE8062: a new combretastatin derivative vascular disrupting agent," Expert Opin Investig Drugs., Oct. 2009, 18(10):1541-1548.
Dong et al., "Experimental studies of portal venous embolization with iodized oil in rats with experimentally induced liver cancer," J Vasc Interv Radiol., Sep. 1993, 4(5):621-624.
Dupeyre et al., "Synthesis and biological evaluation of (3,4,5-trimethoxyphenyl)indol-3-ylmethane derivatives as potential antivascular agents," Bioorg Med Chem., Jul. 2006, 14(13):4410-4426.
Efremidis et al., "Enhancement patterns and signal-intensity characteristics of small hepatocellular carcinoma in cirrhosis: pathologic basis and diagnostic challenges," Eur Radiol., Jul. 2007, 17(11):2969-2982.
Fernandez et al., "Angiogenesis in liver disease," J Hepatol., Mar. 2009, 50(3):604-620.
Foley et al., "The vascular disrupting agent STA-9584 exhibits potent antitumor activity by selectively targeting microvasculature at both the center and periphery of tumors," J Pharmacol Exp Ther., Nov. 2012, 343(2):529-538.
Garon et al., "A randomized Phase II trial of the tumor vascular disrupting agent CA4P (fosbretabulin tromethamine) with carboplatin, paclitaxel, and bevacizumab in advanced nonsquamous non-small-cell lung cancer," OncoTargets Ther., Nov. 2016, 9:7275-7283.
Golfieri et al., "Malignant progression of a small HCC nodule: hypovascular 'early HCC' converted to hypervascular 'small HCC' within six months," Dig Liver Dis., Sep. 2007, 39(9):883-890.
Hinnen et al., "Vascular disrupting agents in clinical development," Br J Cancer., Apr. 2007, 96(8):1159-1165.
Hori et al., "The Combretastatin Derivative (Cderiv), a Vascular Disrupting Agent, Enables Polymeric Nanomicelles to Accumulate in Microtumors," Journal of Pharmaceutical Sciences, Jun. 2010, 99(6):2914-2925.
Iwakiri et al., "Vascular pathobiology in chronic liver disease and cirrhosis—current status and future directions," J. Hepatol., Oct. 2014, 61(4):912-924.
Koh et al., "Reproducibility and changes in the apparent diffusion coefficients of solid tumours treated with combretastatin A4 phosphate and bevacizumab in a two-centre phase I clinical trial," Eur Radiol., Jun. 2009, 19(11):2728-2238.

Landuyt et al., "Vascular targeting of solid tumours: a major 'inverse' volume-response relationship following combretastatin A-4 phosphate treatment of rat rhabdomyosarcomas," Eur J Cancer., Sep. 2000, 36(14):1833-1843.
Li et al., "A dual-targeting anticancer approach: soil and seed principle," Radiology, Sep. 2011, 260(3):799-807.
Li et al., "Diverse Responses to Vascular Disrupting Agent Combretastatin A4 Phosphate: A Comparative Study in Rats with Hepatic and Subcutaneous Tumor Allografts Using MRI Biomarkers, Microangiography, and Histopathology," Translational Oncology, Feb. 2013, 6(1):42-50.
Liu et al., "Mammalian models of chemically induced primary malignancies exploitable for imaging-based preclinical theragnostic research," Quant Imaging Med Surg., Oct. 2015, 5(5):708-729.
Macdonough et al., "Synthesis and biological evaluation of indole-based, anti-cancer agents inspired by the vascular disrupting agent 2-(3'-hydroxy-4'-methoxyphenyl)-3-(3",4",5"-trimethoxybenzoyl)-6-methoxyindole (OXi8006)," Bioorg Med Chem., Nov. 2013, 21(21):50 pages.
Maeda et al., "Vascular permeability in cancer and infection as related to macromolecular drug delivery, with emphasis on the EPR effect for tumor-selective drug targeting," Proceedings of the Japan Academy, 2012, 88(3):53-71.
Mahal et al., "Combretastatin A-4 derived 5-(1-methyl-4-phenyl-imidazol-5-yl)indoles with superior cytotoxic and anti-vascular effects on chemoresistant cancer cells and tumors," Eur J Med Chem., Aug. 2016, 118:9-20.
Maier, "Cirrhosis of the liver as a precancerous condition," Praxis (Bern 1994), 1998, 87(44):1462-1465 (English abstract).
McEvoy et al., "Hepatocellular Carcinoma: Illustrated Guide to Systematic Radiologic Diagnosis and Staging According to Guidelines of the American Association for the Study of Liver Diseases," Radiographics, Oct. 2013, 33(6):1653-1668.
Ng et al., "Phase Ib trial of radiotherapy in combination with combretastatin-A4-phosphate in patients with non-small-cell lung cancer, prostate adenocarcinoma, and squamous cell carcinoma of the head and neck," Ann Oncol., Jan. 2012, 23(1):231-237.
Ni et al., "Magnetic resonance imaging, microangiography, and histology in a rat model of primary liver cancer," Invest Radiol., Sep. 1992, 27(9):689-697.
Nicholson et al., "NPI-2358 is a tubulin-depolymerizing agent: in-vitro evidence for activity as a tumor vascular-disrupting agent," Anticancer Drugs, Jan. 2006, 17(1):25-31.
Nielsen et al., "Non-invasive imaging of combretastatin activity in two tumor models: Association with invasive estimates," Acta Oncol., Oct. 2010, 49(7):906-913.
Park et al., "Neoangiogenesis and sinusoidal "capillarization" in dysplastic nodules of the liver," Am J Surg Pathol., Jun. 1998, 22(6), 13 pages.
Patterson et al., "Vascular damaging agents," Clin Oncol., Aug. 2007, 19(6)443-456.
PCT International Preliminary Report on Patentability in International Appln. No. PCT/EP2018/068141, dated Jan. 7, 2020, 9 pages.
PCT International Search Report and Written Opinion in International Appln. No. PCT/EP2018/068141, dated Aug. 16, 2018, 13 pages.
Rajak et al., "Design of combretastatin A-4 analogs as tubulin targeted vascular disrupting agent with special emphasis on their cis-restricted isomers," Curr Pharm Des., 2013, 19(10):1923-1955.
Schlageter et al., "Histopathology of hepatocellular carcinoma," World J Gastroenterol, Nov. 2014, 20(43):15955-15964.
Shiraishi et al., "Tumor environment changed by combretastatin derivative (Cderiv) pretreatment that leads to effective tumor targeting, MRI studies, and antitumor activity of polymeric micelle carrier systems," Pharm Res., Jan. 2012, 29(1):178-186.
Siemann et al., "A review and update of the current status of the vasculature-disabling agent combretastatin-A4 phosphate (CA4P)," Expert Opin Investig Drugs, Feb. 2009, 18(2):189-197.
Siemann et al., "The vascular disrupting agent ZD6126 shows increased antitumor efficacy and enhanced radiation response in large, advanced tumors," Int J Radiat Oncol Biol Phys., Jul. 2005, 62(3):846-853.

(56) References Cited

OTHER PUBLICATIONS

Sosa et al., "Randomized safety and efficacy study of fosbretabulin with paclitaxel/carboplatin against anaplastic thyroid carcinoma," Thyroid, Feb. 2014, 24(2):1-9.

Sugimoto et al., "Characteristics of Hypovascular versus Hypervascular Well-Differentiated Hepatocellular Carcinoma Smaller Than 2 cm—Focus on Tumor Size, Markers and Imaging Detectability," Digestive Diseases, Oct. 2015, 33(6):721-727.

Tozer et al., "Disrupting tumour blood vessels," Nat Rev Cancer., Jun. 2005, 5(6):423-435.

Wallace et al., "The vascular disrupting agent, DMXAA, directly activates dendritic cells through a MyD88-independent mechanism and generates antitumor cytotoxic T lymphocytes," Cancer Res., Jul. 2007, 67(14):7011-7019.

Wang et al., "Morphological, functional and metabolic imaging biomarkers: assessment of vascular-disrupting effect on rodent liver tumours," Eur Radiol., Aug. 2010, 20(8):2013-2026.

Wang et al., "Treatment of rodent liver tumor with combretastatin a4 phosphate: noninvasive therapeutic evaluation using multiparametric magnetic resonance imaging in correlation with microangiography and histology," Invest Radiol., Jan. 2009, 44(1):44-53.

Yang et al., "Vascular changes in hepatocellular carcinoma," Anat Rec (Hoboken), Jun. 2008, 291(6):721-734.

Zweifel et al., "Phase II trial of combretastatin A4 phosphate, carboplatin, and paclitaxel in patients with platinum-resistant ovarian cancer," Ann Oncol., Sep. 2011, 22(9):2036-2041.

Hori et al., "A novel combretastatin A-4 derivative, AC7700, strongly stanches tumour blood flow and inhibits growth of tumours developing in various tissues and organs," British Journal of Cancer, May 2002, 86:1604-1614.

Hori et al., "In vivo Analysis of Tumor Vascularization in the Rat," Jpn. J. Cancer Res., Mar. 1990, 81:279-288.

Hori et al., "Tumor blood flow interruption after radiotherapy strongly inhibits tumor regrowth," Cancer Sci., Jul. 2018, 99(7):1485-1491.

\* cited by examiner

TREATMENT OF AVASCULAR OR HYPOVASCULAR MICRO-TUMORS

FIELD OF THE INVENTION

The present invention relates to the treatment of avascular and hypovascular tumors.

The present invention further relates to the use of vascular disruption agents in tumor therapy.

BACKGROUND OF THE INVENTION

Combretastatin A4 phosphate (CA4P), as a Combretastatin family member initially derived from the South African willow tree *Combretum caffrum*, has become a leading vascular disrupting agent (VDA) for cancer therapy over the past decades [Tozer et al. (2005) *Nat Rev Cancer.* 5, 423-435; Hinnen & Eskens (2007) *Br J Cancer.* 96, 1159-1165]. CA4P takes effect as a potent and reversible tubulin depolymerizing agent to damage the existing tumor blood vessels [Patterson & Rustin (2007) *Clin Oncol.* 19, 443-456]. In a variety of implanted tumor models conducted in preclinical studies, CA4P induces rapid tumor vascular disruption as early as less than 1 hour resulting in extensive intratumoral necrosis within 12 hours [Cooney et al. (2006) *Nat Clin Pract Oncol.* 3, 682-692; Siemann et al. (2009) *Expert Opin Investig Drugs* 18, 189-197]. Nevertheless, VDA therapy features a viable rim consisting of layers of residual cancer cells at tumor periphery, subsequently leading to tumor relapse over several days Li et al. (2011) *Radiology* 260, 799-807]. This accentuates the necessity to combine CA4P treatment with other therapeutics such as chemotherapy [Bilenker et al. (2005) *Clin Cancer Res.* 11, 1527-1533], conventional radiotherapy [Ng et al. (2012) *Ann Oncol.* 23, 231-237], internal targeted radiotherapy and antiangiogenic therapy [Chen et al. (2012) *PLOS ONE* 7, e41140; Koh et al. (2009) *Eur Radiol.* 19, 2728-2238]. To date, the safety and efficacy of CA4P plus chemo in patients with advanced non-small cell lung cancer [Zweifel et al. (2011) *Ann Oncol.* 22, 2036-2041], anaplastic thyroid cancer and platinum-resistant ovarian cancer have been under evaluations in phase II/III clinical trials.

SUMMARY OF THE INVENTION

The invention is summarized in the following statements.

1. A vascular disrupting agent (VDA) or salt or solvate or prodrug thereof for treating an avascular or hypovascular micro-tumor with a diameter below 20 mm. Typically the microtumors are human microtumors. Since the tumors which are treated in the methods of the present invention are avascular or hypovascular, their size will be inherently limited in view of the limited oxygen and nutrient supply. As detailed below, the maximal size of a micro-tumor depends from animal to animal.

2. The vascular disrupting agent (VDA) or salt or solvate or prodrug thereof according to statement 1 for treating an avascular micro-tumor.

3. The vascular disrupting agent (VDA) or salt or solvate or prodrug thereof for treating a micro-tumor in accordance with statement 1 or 2, wherein the tumor occurs within visceral organs such as liver, spleen, kidney or lung. Specific embodiments exclude the treatment of tumors in the pancreas where the hilum for supplying blood vessels is absent 4. The vascular disrupting agent (VDA) or salt or solvate or prodrug thereof for treating a micro-tumor in accordance with any one of statements 1 to 3, wherein the tumor occurs within cirrhotic or normal liver tissue.

5. The vascular disrupting agent (VDA) or salt or solvate or prodrug thereof for treating a micro-tumor in accordance with any one of statements 1 to 4, wherein the tumor is a human tumor with a diameter of between 1 to 10 mm, or between 1 and 5 mm.

6. The vascular disrupting agent (VDA) or salt or solvate or prodrug thereof for treating a micro-tumor in accordance with any one of statements 1 to 5, wherein the tumor is a grade I to IV tumor as defined by the modified 4 scale Edmondson and Steiner system.

7. The vascular disrupting agent (VDA) or salt or solvate or prodrug thereof for treating a micro-tumor in accordance with any one of statements 1 to 6, wherein the tumor is a grade I or II tumor as defined by the modified 4 scale Edmondson and Steiner system.

8. The vascular disrupting agent (VDA) or salt or solvate or prodrug thereof for treating a micro-tumor in accordance with any one of statements 1 to 7, wherein the tumor is a carcinoma such as a primary hepatocellular carcinoma (HCC) or a sarcoma such as rhabdomyosarcoma.

9. The vascular disrupting agent (VDA) or salt or solvate or prodrug thereof for treating a micro-tumor in accordance with any one of statements 1 to 8, wherein the VDA is a tubulin binding stilbenoid or dihydrostilbenoid.

10. The vascular disrupting agent (VDA) or salt or solvate or prodrug thereof for treating a micro-tumor in accordance with any one of statements 1 to 9, wherein the VDA is combretastatin A-4 (CA4), ZD6126 or STA-9584 or a prodrug, salt or solvate thereof.

Pharmaceutical compositions for treating a micro-tumor in accordance with any of the above statements can further contains an additional anticancer medicaments. The active ingredients can be formulated together or separately. They can be formulated for administration via the same route or via different routes.

11. A method of treating an avascular or hypovascular micro-tumor with a diameter below 20 mm, typically below 10 mm, comprising the step of administering an effective amount of a vascular disrupting agent (VDA) or salt or solvate or prodrug thereof. Such method can be combined or followed by an effective adjunct therapy to reach more curative outcome.

In order to obtain a more curative effect, an intravascular administration of a secondary effective adjunct therapy can be followed once the VDA-induced tumor necrosis is formed typically on the next day after the administration of the VDA agent. Such further therapeutic agent is typically an agent targeting necrotic tissue. A secondary effective adjunct therapy can be performed by an intravascular administration of a targeted radiotherapeutic such as iodine-131 labeled hypericin (which is an exemplary presentative of a small molecular necrosis-avid compounds). These compounds accumulates at the necrotic tumor and emit ionizing radiation such as high energy beta particles with certain penetration distance to kill the adjacent remaining viable cancer cells.

FIGURE LEGENDS

FIG. 1: Flow chart of experimental design. DENA: diethylnitrosamine; HCC: hepatocellular carcinoma; T2WI: T2-weighted imaging; T1WI: T1-weighted imaging; DWI: diffusion-weighted imaging; CE: contrast-enhanced; CA4P:

combretastatin A4 phosphate; n: number of animals; t: number of tumors; Ø: diameter; h: hour (s); iv: intravenous (ly).

Figure 2:
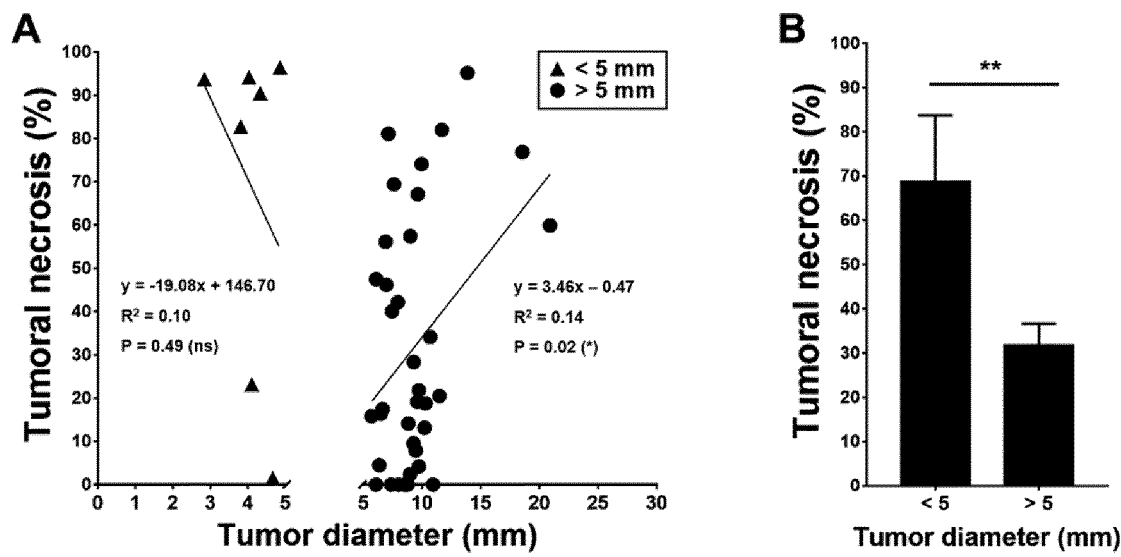

FIG. 2: Comparison of CA4P therapeutic efficacy between micro-HCCs and larger HCCs. A. Scatter plots of percentage of CA4P-induced tumoral necrosis in micro-HCCs≤5 mm and in HCCs>5 mm. Significant negative linear correlation was identified between CA4P-induced tumoral necrosis and tumors with diameter>5 mm (P<0.05), while tumoral necrosis was not linearly correlated with tumors with diameters of ≤5 mm. B. Bar chart comparing the mean percentage of CA4P-induced tumoral necrosis between microHCCs of ≤5 mm and larger HCCs of >5 mm (*P<0.01).

Figure 3:
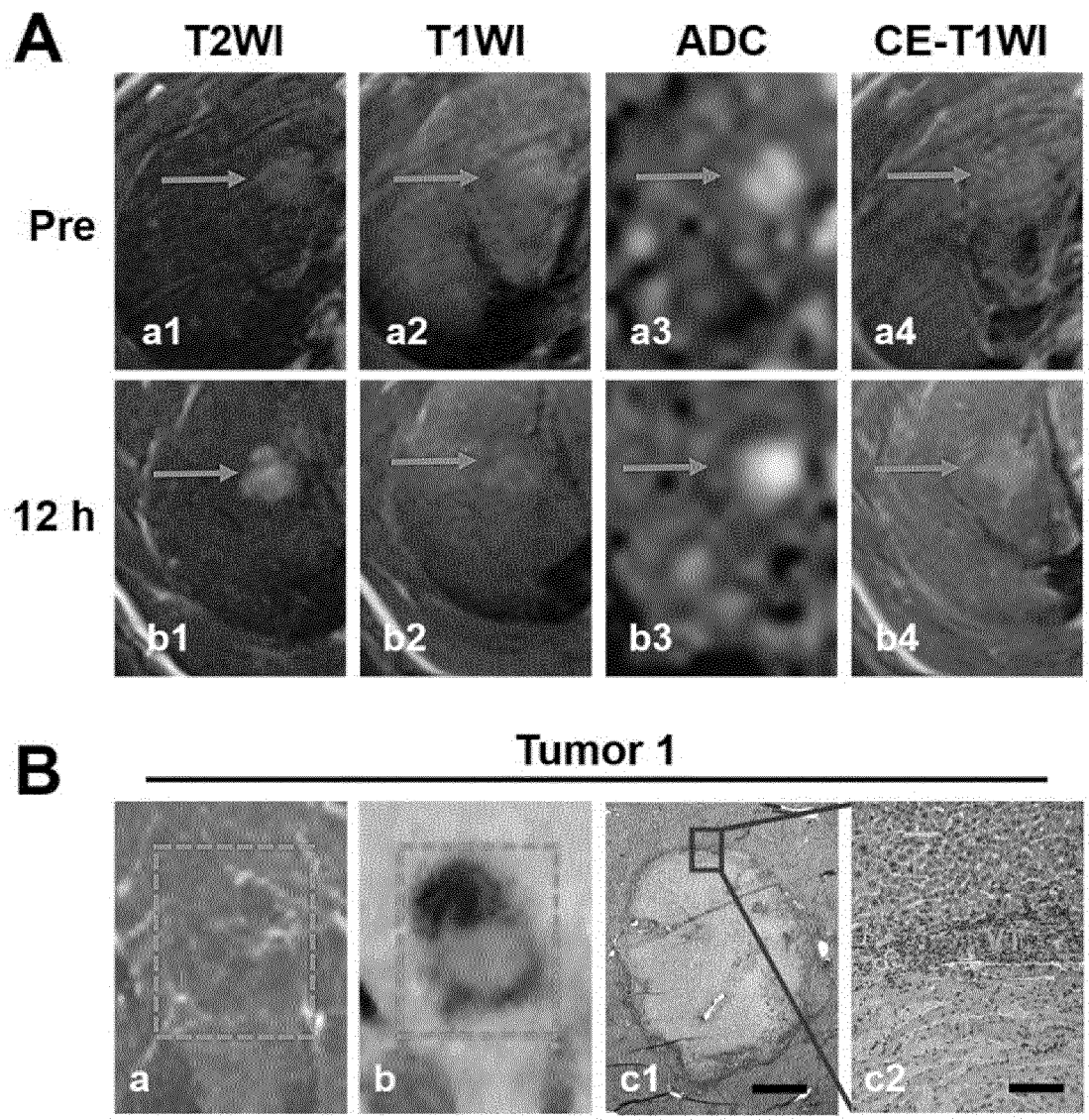
Figure 3:
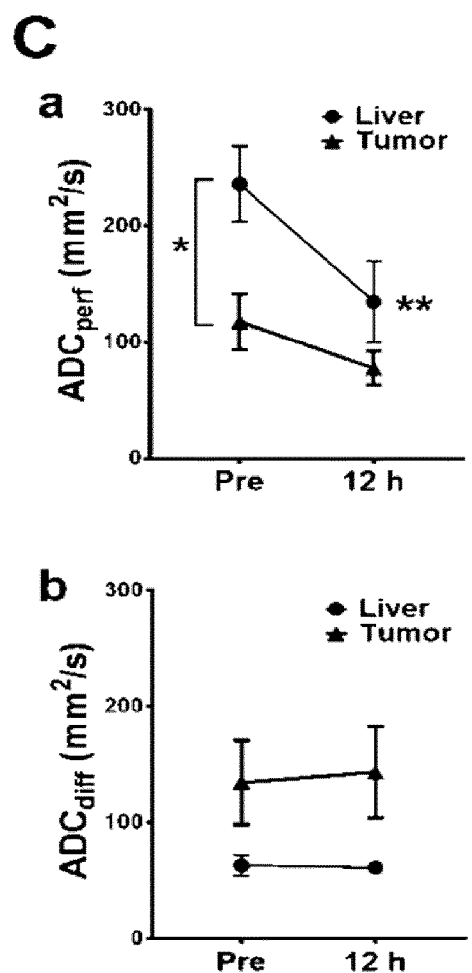

FIG. 3: In vivo MRI and post-mortem verifications of a representative micro-HCC with nearly complete necrosis induced by CA4P. A. In vivo MRI findings of microcancer Tumor 1 (arrows): on T2WI, hyperintense before treatment and increased hyperintensity at 12 h (a1-b1); on precontrast T1WI, there were no obvious changes with nearly isointensity (a2-b2); on ADC map, moderate hyperintense at baseline and increased signal at 12 h (a3-b3); and on CE-T1WI, minimal enhancement at baseline and delayed contrast enhancement at 12 h after CA4P treatment (a4-c4). B. Corresponding microangiography (a1) depicted scarce tumor vascularity. Macrophotograph (b1) and histopathology (H&E staining; c1, ×25 original magnification, scale bar=400 μm; c2, ×200 original magnification, scale bar=50 μm. NT: necrotic tumor; VT: viable tumor; L: liver.) reveal nearly complete intratumoral necrosis. C. Quantification of ADCs derived from DWI. $ADC_{perf}$ (a) indicates blood perfusion sharply decreased in cirrhotic liver after CA4P treatment (P<0.01) with a decline also in tumor. $ADC_{diff}$ (b) slightly increased at 12 h suggestive of CA4P-induced intratumoral necrosis; while liver $ADC_{diff}$ did not show significant change.

Figure 4:
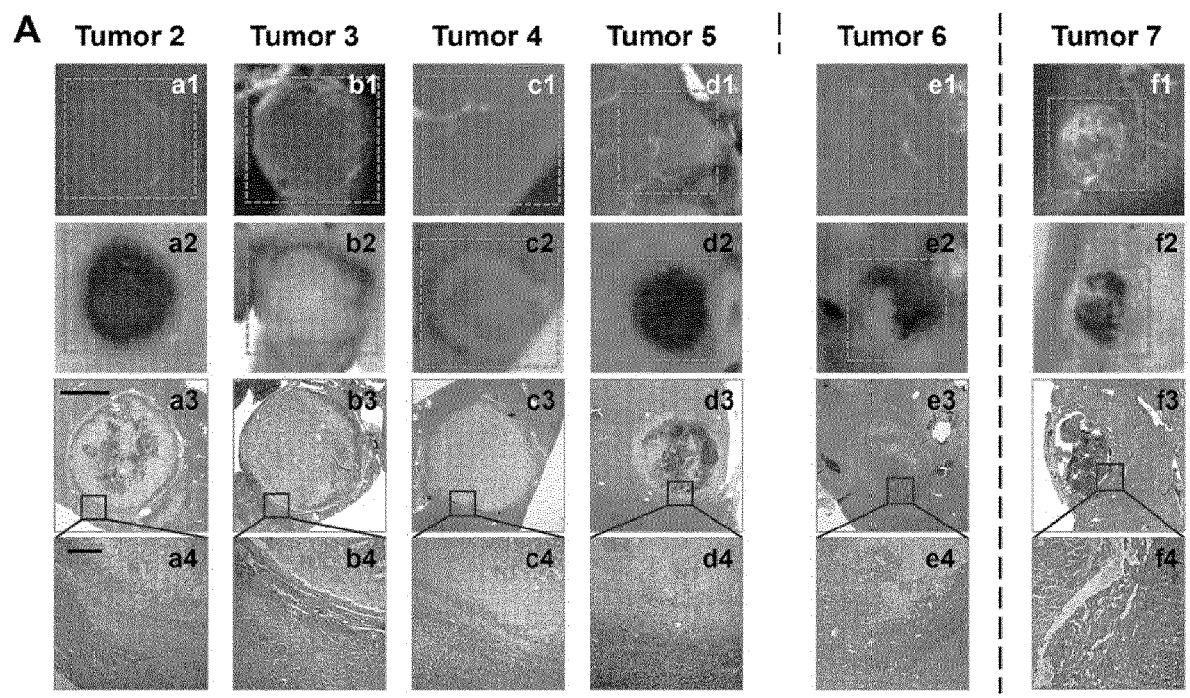
Figure 4:
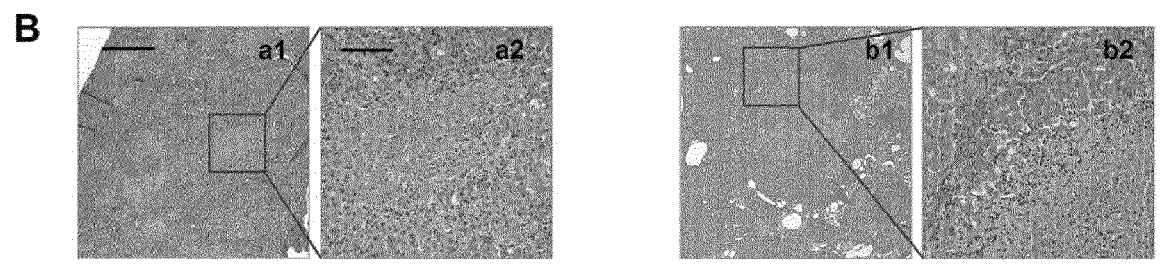

FIG. 4 Post-morterm verifications of CA4P-induced necrosis in micro-HCCs on liver cirrhosis. A. Microangiography (a1-f1) suggested sparser vessel density appeared in Tumor 2-6 where tumoral necrosis occurred, and large vascular lakes existed in Tumor 7 where rare tumoral necrosis was induced; photomacrographs (a2-f2) and microscopies (H&E staining; a3-f3, ×12.5 original magnification, scale bar=800 μm; a4-f4, ×100 original magnification, scale bar=100 μm.) verified nearly complete necrosis occurring in Tumor 2-5, partial necrosis induced in Tumor 6, and rare necrosis in Tumor 7 (NT: necrotic tumor; VT: viable tumor; L: liver; V: vascular lake.). Patchy necrosis (arrowheads) was also scattered in the sounding cirrhotic liver of Tumor 2, 3 and 7. B. Histopathology (H&E staining; a1, b1, ×50 original magnification, scale bar=200 μm; a2, b2, ×200 original magnification, scale bar=50 μm.) demonstrated necrosis foci (arrowheads) existed in the cirrhotic liver parenchyma (NL: necrotic liver; VL: viable liver.).

Figure 5:
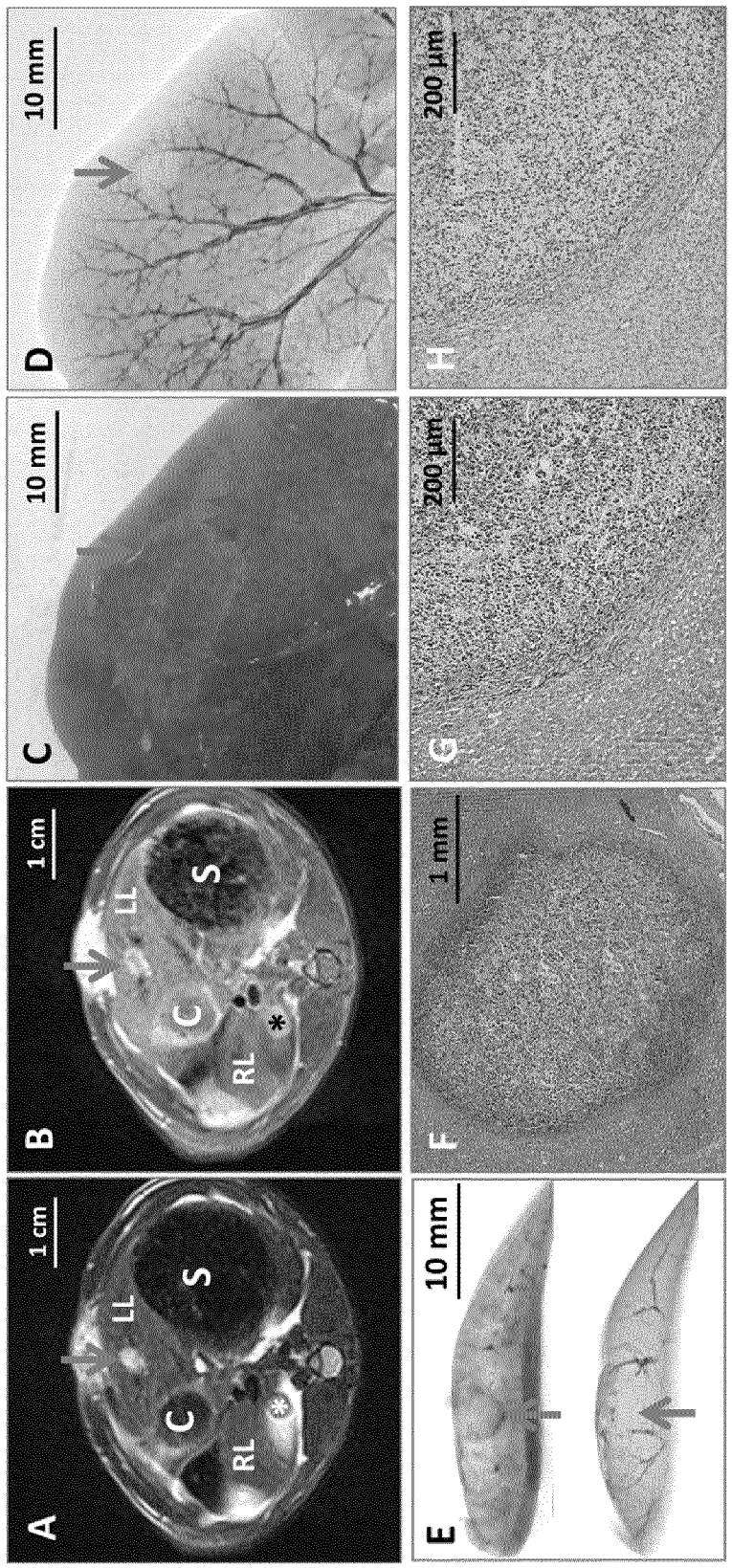

FIG. 5 shows a representative example of 12 h after CA4P treatment in a rat with liver implantation of micro rhabdomyosarcoma R1 tumor of 3.3 and 2.5 in long and short axis diameters. FIG. 5A: on T2 weighted transverse MRI, an oval hyperintense liver lesion (arrow) appears in the left liver lobe (LL); RL, right liver lobe; S, stomach; and C, colon. B: 15 min after contrast agent Gd-DOTA administration, left liver (LL) lesion is enhanced with a central dark region (arrow) suggestive of necrosis; RL, right liver lobe; S, stomach; and C, colon. C: liver specimen containing the micro rhabdomyosarcoma R1 tumor (arrow) that is too small to be seen from the surface. D: corresponding microangiography shows the lesion as a filling defect suggestive of necrosis (arrow). E: the lesion (arrow) can be traced on liver section (upper) and corresponding microangiography (bottom). F: low power HE stained microscopy reveals massive and partial hemorrhagic tumor necrosis with tissue reaction and possible tumor residues at the periphery of this virtually hypo- to avascular R1 tumor. G: higher powered HE stained microscopy clearly depicts the central necrosis and peripheral few layers of viable R1 tumor cells without noticeable intratumoral vasculature. H: corresponding immunohistochemical CD34-PAS dual staining microscopy confirms the findings with HE staining.

Figure 6:
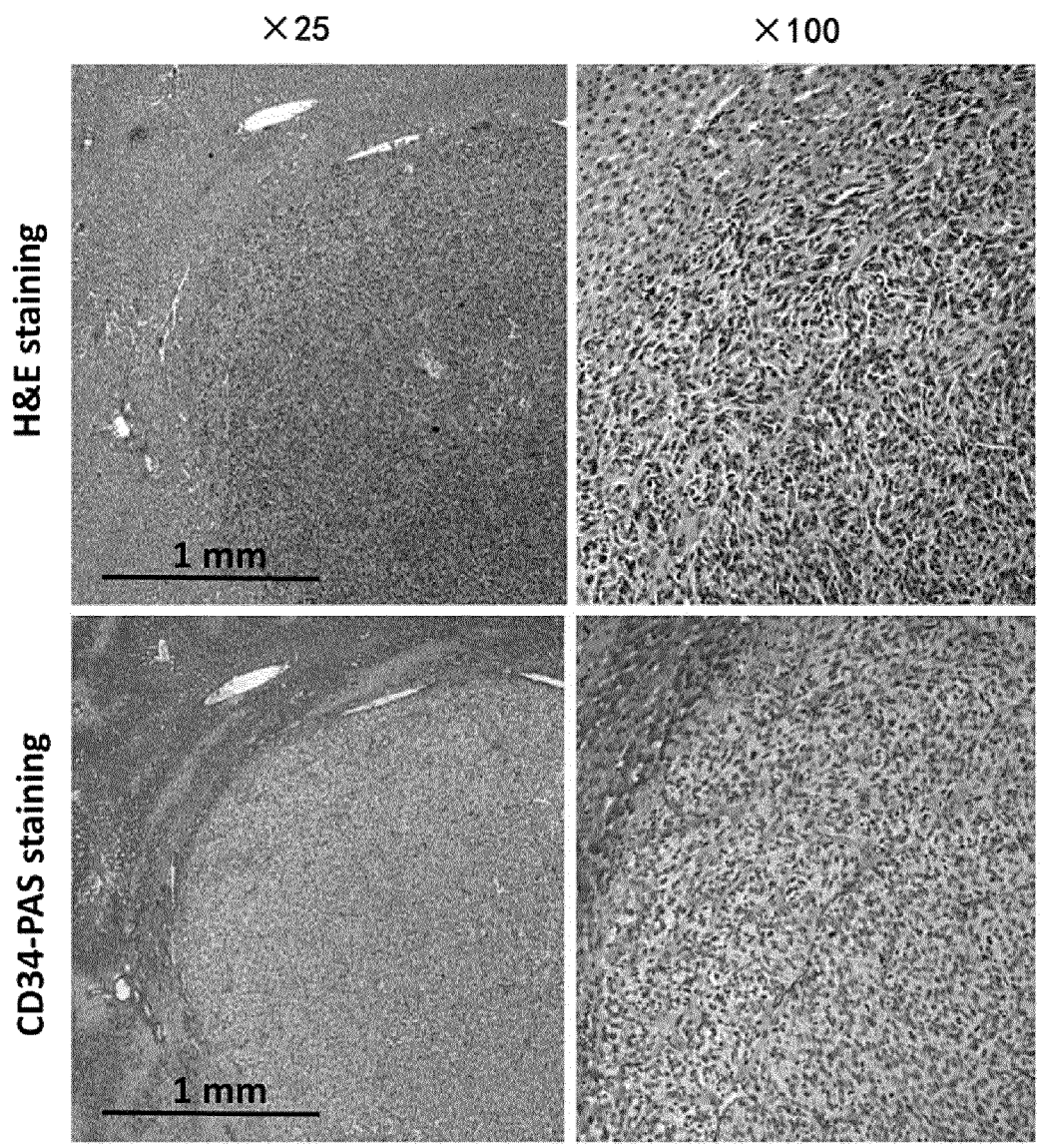

FIG. 6: Histomorphology of micro-tumor without treatment at different magnifications (25 and 100 times). Top panels show staining with hematoxylin and eosin (H&E) staining. Bottom panels show CD34 and periodic acid-schiff (PAS) dual staining.

Figure 7:
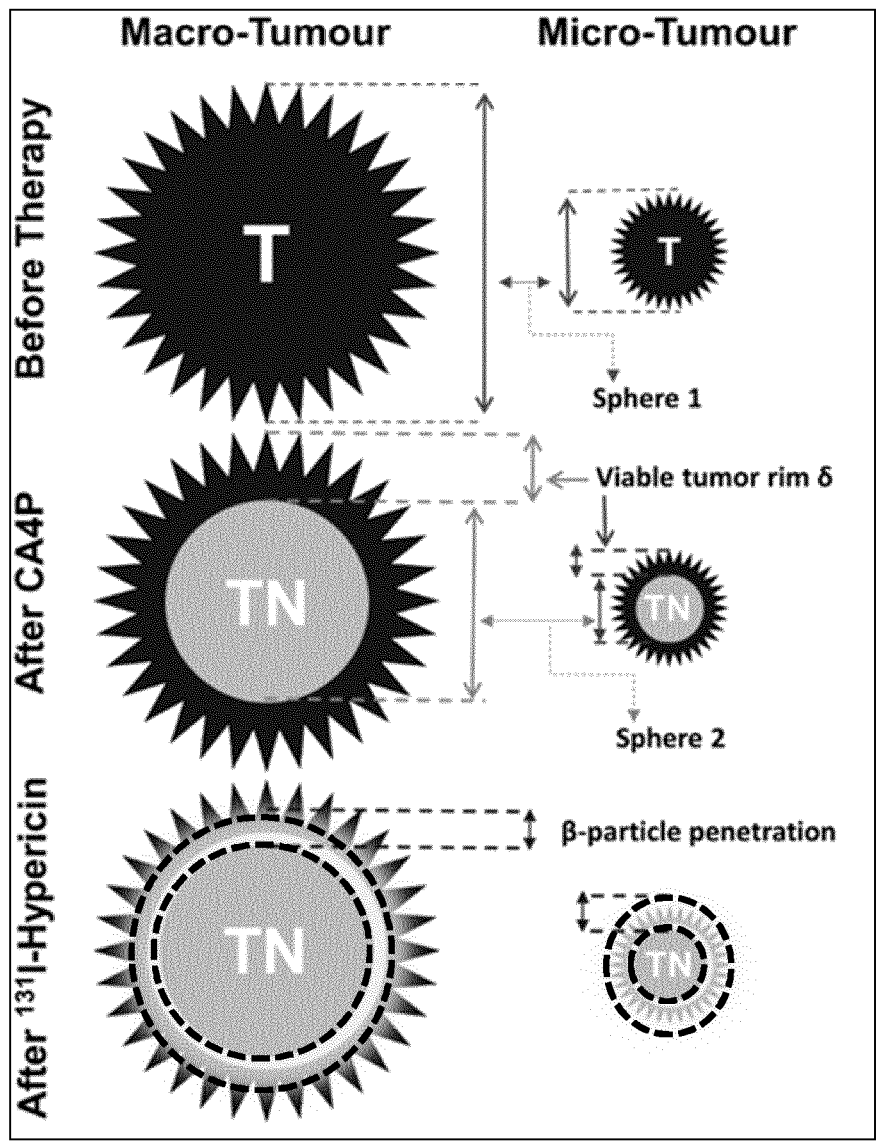

FIG. 7. Schematic therapeutic efficacies between macro- and micro-cancers. Note: T: malignant tumors; TN: CA4P induced tumor necrosis; β particle is about 2.0 mm in penetration (region between dotted lines), which should be greater than δ for a curative effect.

DETAILED DESCRIPTION OF THE INVENTION

Abbreviations Used Throughout the Description

VDA: vascular disrupting agent; CA4P: combretastatin A-4 phosphate; HCC: hepatocellular carcinoma; MRI: magnetic resonance imaging; T2WI: T2-weighted imaging; DWI: diffusion-weighted imaging; CE: contrast-enhanced; T1WI: T1-weighted imaging; ADC: apparent diffusion coefficient; RECIST: Response Evaluation Criteria in Solid Tumors; DCE: dynamic contrast enhanced; DENA: diethylnitrosamine; TSE: turbo spin echo; EPI: echo-planar imaging; SD: Sprague Dawley; ROI: region of interest; SI: signal intensity; H&E: hematoxylin and eosin; SEM: standard errors of the mean.

The following Detailed Description is merely exemplary in nature and is not intended to limit the invention or the application and uses of the invention. Furthermore, there is no intention to be bound by any theory presented in the preceding Background of the Invention or the following Detailed Description.

The following detailed description of the invention refers to the accompanying drawings. The same reference numbers in different drawings identify the same or similar elements. Also, the following detailed description does not limit the invention. Instead, the scope of the invention is defined by the appended claims and equivalents thereof.

Several documents are cited throughout the text of this specification. Each of the documents herein (including any manufacturer's specifications, instructions etc.) are hereby incorporated by reference; however, there is no admission that any document cited is indeed prior art of the present invention.

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn to scale for illustrative purposes. The dimensions and the relative dimensions do not correspond to actual reductions to practice of the invention.

Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

Moreover, the terms top, bottom, over, under and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to the devices consisting only of components A and B. It means that with respect to the present invention, the only relevant components of the device are A and B.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly, it should be appreciated that in the description of exemplary embodiments of the invention, various features of the invention are sometimes grouped together in a single embodiment, figure, or description thereof for the purpose of streamlining the disclosure and aiding the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

In the description provided herein, numerous specific details are set forth. However, it is understood that embodiments of the invention may be practiced without these specific details. In other instances, well-known methods, structures and techniques have not been shown in detail in order not to obscure an understanding of this description.

Other embodiments of the invention will be apparent to those skilled in the art from consideration of the specification and practice of the invention disclosed herein.

It is intended that the specification and examples be considered as exemplary only. Each and every claim is incorporated into the specification as an embodiment of the present invention. Thus, the claims are part of the description and are a further description and are in addition to the preferred embodiments of the present invention.

Each of the claims set out a particular embodiment of the invention.

Particular and preferred aspects of the invention are set out in the accompanying independent and dependent claims. Features from the dependent claims may be combined with features of the independent claims and with features of other dependent claims as appropriate and not merely as explicitly set out in the claims. Thus, the claims following the detailed description are hereby expressly incorporated into this detailed description, with each claim standing on its own as a separate embodiment of this invention.

"Vascular disruption agent" (VDA) in the context of the present invention refers to a functional definition of compounds which target endothelial cells and pericytes of already established tumor vasculature. These compounds differ from antiangiogenic compounds which are used to prevent neovascularization processes in tumors. The general term VDA also encompasses pharmaceutically acceptable salts, solvate, or prodrugs.

The best characterized VDA are tubulin-binding agents and flavonoids.

Tubulin-binding agents work by acting on the [beta]-subunit of endothelial tubulin, resulting in depolymerization of microtubules and disorganization of actin and tubulin. These determine the disruption of the cytoskeleton and of the cell-to-cell junctional protein. These induce a profound change in endothelial cell shape, increased vascular permeability, increased interstitial pressure followed by the inhibition of blood flow and vasoconstriction. The result is a rapid collapse in blood flow, marked ischemia, necrosis and tumor hemorrhage. These effects are more marked in the central areas of tumors.

A specific class of VDA are combretastatins. These are compounds structurally related to combretastatin A4.

All are structurally related to colchicine and include combretastatin A-4 (CA4), its prodrug CA4 phosphate (CA4P), the CA4P analog [3-methoxy-2-phosphonatooxy-6-[(Z)-2-(3,4,5-trimethoxyphenyl)ethenyl] phenyl] phosphate (Oxi4503) (combretastatin A1 phosphate), and (2S)-2-amino-3-hydroxy-N-[2-methoxy-5-[(Z)-2-(3,4,5-trimethoxyphenyl)ethenyl]phenyl] propanamide (AVE8062), methyl-[5-[[4-[[(2S)-2-aminopropanoyl]amino]phenyl]sulfanyl]-1H-benz-imidazol-2-yl]carbamate monohydrochloride (MN-029), N-acetylcochinol-O-phosphate (ZD6126), (3Z,6Z)-3-[(5-tert-butyl-1H-imidazol-4-yl)methylene]-6-(phenylmethylene)-2,5-piperazinedione (NPI-2358), and N-ethyl-N-[2-methoxy-4-[5-methyl-4-[[(1S)-1-(3-pyridinyl)butyl]amino]-2-pyrimidinyl]phenyl]urea. (CYT997).

An example of such analogue is the prodrug ombrabulin which is converted into the active metabolite RPR258063.

In specific embodiments, the VDA is selected from the group consisting of CA4P, ZD6126, and STA-9584.

The following tubulin-binding agents have entered clinical development: CA4P, AVE8062, ABT-751, NPI-2358, Dolastatin-10, MPC6827, CYT997, TZT-1027, ZD6126, BNC105P, EPC2407, MN-029 and Oxi4503.

Numerous VDA's have been described in the art. All VDA mentioned in the above paragraph and disclosed in the below cited documents are incorporated by reference in the present application, and are plausible alternatives for combretastatin A-4 (CA4) and its prodrug CA4 phosphate (CA4P).

A non-limiting list of patent and non-patent literature is listed below.

US93583038 describes VDAs such as colchicine, colchicinoid, combretastatin, phenstatin, podophyllotoxin, steganacin, amphethinile, stilbenes and flavonoids Specific colchicine like molecules are azademethylcolchicine, azacolchicine, N-methyl desacetylcolchicine and desacetylcolchicine.

US2010168036 discloses combretastatin A-4, a combretastatin A-4 phosphate, combretastatin A-1, combretastatin A-1 diphosphate.

US20070178107 discloses combretastatin A-4 disodium phosphate, ZD6126, AVE8062, and Oxi 4503; and the flavonoid, DMXAA.

US20080214509 describes a variety of combretastatin structural analogues, which are explicitly incorporated herein by reference.

Mahal et al. (2016) *Eur J Med Chem.* 118, 9-20 describe Combretastatin A-4 derived 5-(1-methyl-4-phenyl-imidazol-5-yl)indoles.

Macdonough et al. (2013) *Bioorg Med Chem.* 21, 6831-6843 disclose indole-based, anti-cancer agents derived from 2-(3'-hydroxy-4'-methoxyphenyl)-3-(3",4",5"-trimethoxybenzoyl)-6-methoxyindole (OXi8006)

Rajak et al. (2013) *Curr Pharm Des.* 19, 1923-1955 disclose combretastatin cis-restricted isomer analogues.

Foley et al. (2012) *J Pharmacol Exp Ther.* 343, 529-538 disclose the vascular disrupting agent STA-9584.

Shiraishi et al. (2012) *Pharm Res.* 29, 178-186 describe various combretastatin derivatives.

Delmonte & Sessa (2009) *Expert Opin Investig Drugs.* 18, 1541-1548 disclose AVE8062, a new combretastatin derivative.

Nicholson et al. (2006) *Anticancer Drugs* 17, 25-31 disclose NPI-2358 a tumor vascular-disrupting agent.

Wallace et al. (2007) *Cancer Res.* 67, 7011-7019 disclose the vascular disrupting agent DMXAA.

Dupeyre et al. (2006) *Bioorg Med Chem.* 14, 4410-4426 disclose (3,4,5-trimethoxyphenyl)indol-3-ylmethane derivatives as antivascular agents.

An example of a VDA flavonoid is the flavone-8-acetic acid analogue ASA404 (vadimezan).

Other compounds which target tumor vasculature include ligand-directed VDAs [endo-TAG (cationic lipid paclitaxel), ADH-1 exherin, cytokines such as tumour homing peptide-TNF, cytotoxics such as paplitaxel.

Equally envisaged are a pharmaceutically acceptable salt, solvate, or prodrug of the above mentioned compounds.

The compounds described herein may be administered as compounds per se or may be formulated as medicaments. The medicaments/pharmaceutical compositions may optionally comprise one or more pharmaceutically acceptable excipients, such as carriers, diluents, fillers, disintegrants, lubricating agents, binders, colorants, pigments, stabilizers, preservatives, antioxidants, or solubility enhancers.

The specific dose level and frequency of dosage for any particular individual subject may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the individual subject undergoing therapy.

The compounds disclosed herein can be used in combination with other therapeutic agents, in particular with other anticancer drugs.

A VDA is typically administered by intravenous or intraperitoneal administration. It is known in the art the certain VDA can be administered orally.

Doses of the drug and frequency of administration of the drug are assessed in animal models and clinical trials and depend from parameters such as the size of the tumor, grade of the tumor, adverse effects and the eventual co-administration with other drug.

"Microcancer" or "micro-tumour" in the context of the present invention refers to tumours in rats with a diameter below 5 mm. Microcancers or microtumors in humans (or larger animals such as horses, non-human primates, and cattle) refers to tumours with a diameter below 20 mm, below 15 mm, or below 10 mm.

"Avascular" or "hypovascular" tumor refers to malignant tissue mass with respectively no obvious blood vessel, or less blood vessels than that in the corresponding healthy tissue. This is in contrast with a hypervascular tumor which has a more blood vessels than that in its corresponding healthy tissue.

Specific embodiments of the present invention relate to the treatment of avascular or hypovascular hepatocellular carcinomas (HCCs) including vaguely nodular, differentiated tumors ("early" HCCs), and to distinctly nodular lesions with similar histological feature to "classic" large HCCs (small HCCs of distinctly nodular type), or metastatic tumors to the liver or tumors in organs other than the liver.

"Treatment" in the context of the present invention refers to an improvement of the health status of the subject under treatment, and includes a delayed growth of a tumor, preventing the growth of a tumor and typically a shrinking of a tumor. Other indications of an improvement of the health status include the occurrence of necrosis in the tumor, disappearance of tumors or metastasis, or a classification of the tumor into a less severe tumor grade classification.

Anti-cancer activity of vascular disrupting agents (VDAs) features tumoral necrosis surrounded by residual cancer cells and a 'positive' volume-response relationship. We investigated the efficacy of a VDA combretastatin A-4 phosphate (CA4P) in relation to tumor size of hepatocellular carcinomas (HCCs) in rats using magnetic resonance imaging (MRI) and postmortem techniques. Nineteen rats were chemically-induced with 43 primary HCCs of 2.8-20.9 mm in diameter on liver cirrhosis. They received CA4P intravenously at 10 mg/kg. Tumor diameter was measured by T2-weighted imaging (T2WI) to define microcancers (Ø<5 mm) versus larger HCCs. Vascular responses and tissue necrosis were detected by diffusion-weighted (DWI) and contrast-enhanced T1-weighted imaging (CE-T1WI), which were validated by microangiography and histopathology. DWI-derived apparent diffusion coefficient (ADC) map and CE-T1WI revealed nearly complete necrosis in 5 out of 7 micro-HCCs, but diverse therapeutic necrosis in larger HCCs with a positive correlation with tumor size. Necrosis in micro-HCCs was 36.9% more than that in larger HCCs. $ADC_{perf}$ indicated sharply decreased blood perfusion in cirrhotic liver with a drop also in micro-HCCs. $ADC_{diff}$ increase suggested tumoral necrosis, with cirrhotic liver being nearly unchanged. Microangiography and histopathology revealed massive, partial and minor degrees of tumoral necrosis in 5, 1 and 1 microcancers respectively, and patchy necrotic foci in cirrhotic liver. In this study, more complete CA4P-response occurred unexpectedly in micro-HCCs in rats, along with CA4P-induced necrotic foci in cirrhotic liver. MRI enabled detection of vascular reaction and tumoral necrosis. These may help planning clinical applications of VDAs in patients with HCCs and liver cirrhosis.

Relative to other chemotherapies, an 'inverse' volume-response relationship following VDA treatment has been noticed, since the antitumor efficacy of VDAs seemed to increase as tumors grew larger [Garon et al. (2016) Onco-Targets Ther. 9, 7275-7283]. Such a correlation between increasing tumor size and better therapeutic effect of VDAs has been observed in multiple murine allograft and xenograft models in preclinical studies [Nielsen et al. (2010) Acta Oncol. 49, 906-913; Landuyt et al. (2000) Eur J Cancer. 36, 1833-1843; Siemann & Rojiani (2005) Int J Radiat Oncol Biol Phys. 62, 846-853]. For instance, in the rat allograft model of subcutaneous rhabdomyosarcomas, CA4P efficacy in large tumors ($\geq 14$ cm$^3$) was 16.6-fold stronger than that in small tumors ($<1$ cm$^3$). Similarly, intraperitoneal injection of ZD6126 led to nearly 90% necrosis in tumors larger than 1 g compared with only ~25% in the smaller ones of less than 0.3 g in several mouse xenograft models including rodent sarcoma, squamous cell carcinoma and fibrosarcoma, as well as human renal cell carcinoma, Kaposi's sarcoma and breast carcinoma. Furthermore, this trend has also been implied in the clinical studies of advanced anaplastic thyroid carcinoma [Sosa et al. (2013) Thyroid 24, 232-240]. Despite these strong evidences, the underlying mechanisms remain to be unraveled. The inferior effects of VDAs in small tumors are likely due to their main portions of blood supply largely rooting from the vessels of the surrounding normal tissues [Dong & Lin (1993) J Vasc Intery Radiol 4, 621-624] Indeed, tumors smaller than 5 mm in diameter often lack their own vasculature and are nourished by the nutrients diffused from their host organs.

As CA4P causes acute tumoral necrosis within hours, the conventional imaging criteria, Response Evaluation Criteria in Solid Tumors (RECIST), routinely adopted at the end points of VDA trials cannot fully meet the growing needs of detecting early and transient tumor vascular reaction occurring prior to the change of tumor size. Magnetic resonance imaging (MRI) is known to be of high sensitivity and excellent soft tissue contrast to identify rat liver tumors as small as 2 mm [Ni et al. (1992) Invest Radiol 27, 689-697]. To date, multiparametric methods including dynamic contrast enhanced (DCE)-MRI and diffusion-weighted imaging (DWI) have been increasingly applied in both preclinical and clinical studies for acquiring functional information such as blood perfusion, fluid diffusion, blood volume, vascular permeability and extravascular extracellular space and for noninvasively monitoring the real-time vascular responses [Wang et al. (2009) Invest Radiol. 44, 44-53; Wang et al. (2010) Eur Radiol. 20, 2013-2026].

In the present study, we employed a chemically induced primary liver cancer or hepatocellular carcinomas (HCCS) model in rats, and evaluated the therapeutic efficacy of CA4P against HCCs in differential sizes, especially in the hepatic microcancer lesions in diameter ranging from 2 to 5 mm. Translationally, a 3.0T clinical MRI with a human wrist coil was utilized to characterize the in vivo early vascular responses to CA4P within 12 hours, and the imaging findings were further verified by ex vivo microangiography and histopathology.

The development of HCCs in the cirrhotic liver is characterized by multistep remodeling of tumor blood supply [Yang & Poon (2007) Anat Rec 91, 721-734.]. HCCs are generally hypervascularized solid tumors that are fed predominantly by hepatic arterial branches [Park (1998) Am J Surg Pathol. 22, 656-662]. But, small HCCs in human patients ($<2$ cm) are frequently not hypervascular [Golfieri R, et al. (2007) Dig Liver Dis. 39, 883-890] and can be further divided into two types, namely vaguely nodular, well-differentiated tumor ("early" HCC), and distinctly nodular lesion with similar histological feature to "classic" large HCC (small HCC of distinctly nodular type) [Efremidis et al. (2007) Eur Radiol. 17, 2969-2982]. Likewise, in DENA-induced rat liver cancer, it has been shown that hepatic tumor nodules smaller than 5 mm are fundamentally supplied by the portal vein, which is distinguishing from the large rat HCCs. Given the diverse HCC vascularity, it would be valuable to analyze the early HCCs as a subgroup of micro-HCCs.

In this preclinical study, we reported for the first time that nearly complete CA4P therapeutic responses in the microcancers ($<5$ mm) of DENA-induced primary HCCs in rats, along with treatment-induced necrotic foci scattered on the cirrhotic liver background. Perfusion and diffusion calculated from ADC helped to portray early tumoral vascular reaction and necrosis, secondary to the dramatic fall of entire liver blood supply. Two main factors may synergistically contribute to this superior efficacy of CA4P in microcancers, 1) avascular and/or hypovascular features in such "early HCCs", "small HCCs" or micro-HCCs; and 2) neovascularization in cirrhotic liver parenchyma also vulnerable to CA4P mediated antitubulin effects. Consequently, vascular shutdown and ischemic necrosis in the host liver could render the micro-HCCs deprived from vital nutrition, leading to the present paradoxical findings.

Liver cirrhosis has been widely considered as a high-risk precancerous condition which could be due to chronic viral hepatitis, alcohol, aflatoxin, etc. [Maier K P. (1998) Praxis 87, 1462-1465; Schlageter et al. (2014) World J Gastroenterol 20, 15955-15964]. Application of carcinogen DENA in rodents could simulate this pathological progression and eventually induces primary liver cancers with underlying liver cirrhosis [Liu (2015) Quant Imaging Med Surg. 5, 708-729]. Development of liver fibrosis is associated with pathological angiogenesis that progressively forms the abnormal angioarchitecture distinctive of cirrhotic liver [Fernandez et al. (2009) J Hepatol. 50, 604-620; Iwakiri et al. (2014) J. Hepatol. 61, 912-924]. Notably, CA4P-induced necrosis in cirrhotic liver as seen in our study indicates that neo-angiogenesis in liver fibrogenic progress might share something in common with tumor angiogenesis that can be equally targeted by VDAs. However, our supplementary study on normal liver with implanted R1 tumor does not seem to support the hypothesis that the attack of CA4P on cirrhotic liver with neo-vasculature could be responsible to the secondary massive necrosis in those micro-cancers. The real mechanisms underlying such puzzling observations need to be further elucidated.

Although DWI has been a renowned imaging marker to monitor early VDA-induced tumor vascular responses and further indicate tumoral necrosis, the calculated ADC changes concerning tumor perfusion and diffusion in our study did not appear so significantly. The associated reasons might be the increased MRI artifact when tumor volume is too small, and the limited cases of recruited hepatic microcancers in this study. Secondly, considering the significant alterations of blood supply in the cirrhotic liver and the lack of reports regarding such side effect of VDA in liver cirrhosis in the clinical studies, it would be valuable to conduct parallel studies to compare VDA effects in normal and cirrhotic livers.

On balance, the present findings shed light on the preventative effect of CA4P on recurrent hepatoma foci as well as intrahepatic micrometastases in cirrhotic background. But on the other hand, such a phenomenon also raise the awareness to protect liver function during future CA4P therapy principally in patients with underlying chronic hepatic diseases being developed into cirrhosis, for potential formation of CA4P-induced necrosis in cirrhotic liver and consequent liver failure. These may be of potential value for planning further clinical applications of CA4P in human subjects with HCCs and liver cirrhosis.

The discovery of potent efficacy of VDAs such as CA4P in micro-cancers could be of great significance in clinical management of cancer patients. In particular, knowing that VDA mono-therapy has proven ineffective, combined necrosis-targeting dual therapy requires to minimize residual cancer tissue to exert potentially curative response. Our studies on micro-cancers of both primary HCCs and secondary rhabdomyosarcoma R1 tumors suggest that the prior-art dual therapy may achieve more thorough therapeutic outcomes, because the remaining viable tumor cells are really minimum at the periphery, which are well within the 2 mm penetration distance of the high energy β particles emitted from $^{131}$I-iodinated necrosis avid small molecules such as hypericin. Therefore, instead of being used in late stage cancer patients as a tumor-mass reducing palliative measure, such a dual targeting therapy could yield curative outcomes if it can be applied at very early stage, i.e. micro-cancer stage.

EXAMPLES

General Condition

In total, 43 primary HCC lesions were successfully generated in the 19 rats. Among them, 7 rats were identified with one mocro-HCC each. All rats survived the experimental procedures including diethylnitrosamine (DENA) gavage for hepatocarcinogenesis, gas anesthesia, MRI scanning with contrast administration, and intravenous CA4P treatment. All rats were sacrificed 12 h after CA4P treatment as the endpoint of in vivo study.

A 'Positive' Volume-Response Relationship in Larger HCCs

We first compared CA4P-induced tumoral necrosis among 43 HCCs in various tumor diameters to investigate the relationship between antitumor efficacy of CA4P and tumor size of primary HCCs (FIG. 1). In line with the previous studies that CA4P showed increased activity in larger tumors, CA4P efficacy in this study appeared positively correlated with the larger HCCs with diameters ranging from 5.7 mm to 20.9 mm, though showing great disparities in proportion of therapeutic necrosis (FIG. 2A).

Paradoxical Effects of CA4P in Hepatic Microcancers

Surprisingly, extensive therapeutic tumoral necrosis frequently occurred in a subgroup of smaller HCCs, namely hepatic microcancers, which were smaller than 5 mm in diameter (FIG. 2A). Tumoral necrosis ranging from 80% to nearly 100% was found in 5 out of 7 microcancer lesions. Quantitatively, the rate of tumoral necrosis in the hepatic microcancers was 36.93% higher than that in the larger HCCs after CA4P treatment (FIG. 2B).

The early dramatic reactions in hepatic microcancers could be detected by real-time multiparametric MRI, as demonstrated by a representative hepatic microcancer Tumor 1 (FIG. 3A). At baseline, the microcancer appeared slightly hyperintense on T2WI (FIG. 3Aa1), nearly isointensity on T1WI (FIG. 3Aa2), moderately hyperintense on ADC map (FIG. 3Aa3) and nearly unenhanced on CE-T1WI, suggestive of hypovascularity (FIG. 3Aa4). Twelve hours after CA4P treatment, massive tumoral necrosis was induced, revealed by the strong hyperintensity within entire tumor on T2WI (FIG. 3Ab1), increased tumor ADC (FIG. 3Ab3), and delayed contrast enhancement on CE-T1WI (FIG. 3Ab4) compared with the precontrast T1WI (FIG. 3Ab2). These imaging findings were validated by post-mortem microangiographic and histopathologic assessments (FIG. 3B). Microangiography depicted the reduced tumor vessel density (FIG. 3Ba). Gross specimen of tumor-bearing liver tissue (FIG. 3Bb) and corresponding H&E stained photomicrograph confirmed the nearly complete tumoral necrosis superimposing on the cirrhotic liver (FIG. 3Bc1, 3Bc2).

Blood Perfusion Drop in Cirrhotic Liver Attributable to Massive Necrosis in Microcancer?

Given the general consensus that small tumors tend to poorly respond to VDA treatment due to the lack of their own established vasculature, we next examined our hypothesis that the blood supply in the surrounding cirrhotic liver had been affected by CA4P as well and, therefore, it caused secondary ischemic necrosis in microcancers. Vascular behaviors both in the tumor and the surrounding cirrhotic liver were assessed by ADC calculations. Quantitative $ADC_{perf}$ indicated that, first at baseline, cirrhotic liver appears significantly hyperperfused relative to micro-HCCs ($p<0.05$); secondly, CA4P sharply decreased blood perfusion in the surrounding liver ($p<0.05$) with consequent drop of tumor perfusion (FIG. 3Ca). This finding suggests that vasculature of cirrhotic liver was also severely affected by CA4P, resulting in continuous liver ischemia for at least 12 h and a secondary damage to hepatic microcancers that totally rely on the supply from the surrounding liver. Meanwhile, tumor $ADC_{diff}$ slightly rose, but was nearly unchanged in the surrounding liver, suggestive of tumoral necrosis formation (FIG. 3Cb).

Massive Necrosis in Hepatic Microcancer Along with Scattered Necrosis in Cirrhosis Liver By histopathologic and microangiographic analyses, the tumor reactions to CA4P therapy was further compared in all those 7 microcancers. Consistently, nearly complete necrosis (82.77-96.45%) was induced in the hypovascular Grade I-II well-differentiated micro-HCCs, i.e. Tumor 1-5 (FIG. 3B; FIG. 4Aa1-a4, 4Ab1-b4, 4Ac1-c4, 4Ad1-d4); while partial tumoral necrosis (23.15%) was seen in the hypervascular Grade III poorly differentiated Tumor 6 (FIG. 4Ae1-e4) and minimal necrosis in Grade IV undifferentiated Tumor 7 that was composed largely with vascular lakes (FIG. 4Af1-f4). On top of that, necrotic foci scattered in the cirrhotic liver as seen by microscopy with neovasculature in cirrhotic parenchyma that could also be affected by CA4P treatment (FIG. 4B).

Micro-Cancers Targetable by Vascular Disrupting Agents

The state of the art indicates that tumors could not enlarge beyond millimeter diameters without recruiting new capillary blood vessels (i.e. neoangiogenesis), and that VDAs treat cancers by destroying existing aberrant tumoral vessels, which means that tumors smaller than a few millimeter (pre-neovascularization stage) will not be affected by VDAs to result in tumor necrosis. This is the main reason why so far all in vivo studies on VDAs have been conducted in animal models with tumor masses around or larger than 1 cm in diameter. To handle minute tumors in rodent visceral organs presents another reason. For the first time to our knowledge, we tested a VDA CA4P in rats with chemically induced multifocal hepatocellular carcinomas (HCCs) of diverse tumor sizes and degrees of malignancy, which gave us a chance to look into the performance of CA4P among micro-HCCs of 2-5 mm in size. Surprisingly, we found that 5 out of 7 HCCs were necrotized over 80% by CA4P, all of which are avascular or hypovascular differentiated HCCs, and the rest two are hyper-vascularized with much less proportions of therapeutic necrosis.

To verify whether the above unexpected findings can be supported in other types of solid tumors, we intentionally studied CA4P in a group of rats with liver implantation of rhabdomyosarcomas (R1) ranging from 1 to 5 mm in diameter as monitored by noninvasive longitudinal MRI and verified by postmortem techniques. R1 has been extensively studied on VDA research before but in much larger tumor size. Consistently, 10 out of 11 such lesions showed over 90% necrosis and all of them can be rated as either avascular or hypovascular tumors as exemplified by FIG. 5.

To gain insight into the puzzle why those micro-cancers responded well to a VDA despite a lack of clear tumoral vascularity, histology comparing standard HE staining and immune-histochemical staining was performed as demonstrated in FIG. 6. Microscopic views of a micro-tumor in the liver show that by conventional hematoxylin and eosin (H&E) staining (upper row) the tumor appears to be avascular or hypovascular, i.e. without a clear vascular structure, which could be attributed to the notion that VDAs such as CA4P do not work in small or micro-cancers because of a lack of tumor vasculature. However, by immunohistochemical CD34 and periodic acid-schiff (PAS) dual staining (lower row), positively stained neoangiogenic endothelia can be densely identified forming a network of cells throughout the tissue. These cells appear to be the target of VDAs and can explain nearly complete tumor necrosis in our experiments with small or micro-cancers.

To foresee the curative probability in micro-cancers by combined VDA and a radiolabeled necrosis-avid compound such as $^{131}$I-Hypericin ($^{131}$I-Hyp), we performed mathematical modeling as shown in FIG. 7.

The formula for the volume of the sphere 1 of radius $r_1$ is $V_1 = 4/3\pi r_1^3$; for the volume of the sphere 2 of radius $r_2$ is $V_2 = 4/3\pi r_2^3$; suppose $V_2$ is $\alpha$ % of $V_1$ (e.g. 0.8=80%): $V_2 = \alpha V_1$; that is $4/3\pi r_2^3 = \alpha 4/3\pi r_1^3$; thus $r_2^3 = \alpha r_1^3$, $r_2 = r_1 \sqrt[3]{\alpha}$; the thickness of viable tumour rim $\delta$ will be:

$$\delta = r_1 - r_2 = r_1 - r_1\sqrt[3]{\alpha} = r_1(1 - \sqrt[3]{\alpha}).$$

A VDA or CA4P is known to be able to induce 50-99% ($\alpha$) of tumour necrosis. Upon the calculations by the above formulae, only less than 10% of macro-cancers of 2-10 cm in diameter may achieve curative efficacy by intravenous administrations of CA4P and $^{131}$I-Hyp once consecutively in two days, while the majority tumors show a palliative effect. However, nearly all micro-cancers less than 2 cm in diameter could be eradicated by only once such dual iv deliveries (FIG. 7).

As depicted in FIG. 7, a macro tumor still contains after VDA treatment a considerable layer of surviving cells which receive oxygen and nutrients from the surrounding tissue. The radioactive medicament which binds to the necrotic tissue only emits radiation to a certain extent (region between dotted lines in FIG. 7) Cells outside this region survive and lead to a relapse.

In the micro tumor the entire region of surrounding surviving cells can be irradiated leading to a complete eradication of the tumor.

To prove the principle of such curative efficacy among micro-cancers by this combined dual targeting approach, the following experimental protocols are applied: 1) Multi-species animal models involve rabbits with liver implanted VX2 tumors and rats with liver implanted R1 tumors in groups (n=10 each) of blank control, single targeted and dual targeted treatment; 2) Magnetic resonance imaging (MRI) monitors tumor growth and therapeutic efficacies; 3) treatments include CA4P 20 mg/kg iv, $^{131}$I-hyp iv at 2 mCi/kg and normal saline as control; and 4) the end-points are a) overall animal survivals, b) tumor size measured by in vivo MRI and histopathology, and c) autoradiography for proof of targetability, as compared at different time points among groups.

Materials and Methods

Animals and Reagents

Male Sprague Dawley (SD) rats were purchased from Charles River Breeding Laboratories, Inc. (St. Aubain les Elbeuf, France). Diethylnitrosamine (DENA, N0258) was procured from Sigma-Aldrich (St. Louis, Mo., USA). CA4P (C643025) was obtained from Toronto Research Chemical Inc. (Toronto, Canada). MRI contrast agent Dotarem (Gd-DOTA, Gadoterate meglumine; Dotarem®, Guerbet, France), barium sulfate suspension (Micropaque®, Guerbet, France) and gas anesthetic isoflurane (Forane®; Baxter Healthcare, Deerfield, Ill.) were also commercially obtained.

In Vivo MRI

Images were acquired on a clinical 3.0T MRI scanner (MAGNETOM Prisma; Siemens, Erlangen, Germany) and a human wrist coil (Hand/Wrist 16, A 1.5 T Tim coil, Siemens). Twenty axial images were acquired, with a slice thickness of 2.0 mm and a gap of 0.4 mm. T2-weighted (repetition time, 4000 ms; echo time, 70 ms; flip angle, 150°; field of view, 75×56 mm$^2$; matrix, 256×192) and T1-weighted (repetition time, 626 ms; echo time, 15 ms; flip angle, 160°; field of view, 75×56 mm$^2$; matrix, 256×192) turbo spin echo (TSE) images (T2WI, T1WI) were performed weekly to monitor tumor growth, while T2WI, T1WI, diffusion-weighted imaging (DWI) and consecutive contrast-enhanced (CE-) T1WIs were acquired to evaluate CA4P treatment. For DWI, a 2-dimensional SE echo-planar imaging (EPI) sequence (repetition time, 3500 ms; echo time, 62 ms; flip angle, 90°; field of view, 136×74 mm2; matrix, 96×52) with 8 b values (0, 50, 100, 150, 400, 600, 800 and 1000 seconds/mm$^2$) was acquired. For CE-MRI, a bolus of 0.2 mmol/kg Gd-DOTA was injected before a series of CE-T1WIs were acquired.?

Experimental Design

This animal experiment was carried out in compliance with European and national regulations after approval from KU Leuven university ethics committee for animal care and use. All in vivo procedures including gavage feeding, tumor implantation, drug injection and imaging were performed under gas-anesthesia with 2% isoflurane in the mixture of 20% oxygen and 80% room air using a gas anesthesia system (Harvard Apparatus, Holliston, Mass.).

As illustrated in FIG. 1, multifocal primary liver cancers were established in 19 male Sprague Dawley (SD) rats weighting 300-350 g by 8-week daily gavage feeding of DENA at 10 mg/kg/day. Tumor growth was monitored weekly by MRI from the 9th week after DENA administration until the largest tumor lesion attained more than 1 mm in diameter. All recruited tumor-carrying rats received single intravenous injection of CA4P at 10 mg/kg. T2WI, T1WI, DWI and CE-T1WI were performed 4 h before and 12 h after CA4P therapy. Rats were euthanized after the last time point of MRI for postmortem microangiography and histopathology.

MR Image Analyses

Image analysis was conducted using the built-in software on the Siemens workstation (version Numaris/4 Syngo MR A30) and MeVisLab (version 2.6.2, MeVis Medical Solutions AG, Bremen, Germany). All the following measurements were acquired by 3 authors with consensus.

1) Measurement of Tumor Diameter

On T2WI, tumor diameter was manually measured from the tumor-containing image with the largest tumor cross section at 4 h before treatment.

2) Separate Calculation of Tumor ADCs

On DWI, tumor area was manually contoured with an operator-defined region of interest (ROI) on all tumor-containing images. ADC map was calculated from DWI to quantify therapeutic responses by the following mono-exponential formula: $S_i=S0 \times \exp(-b_i \times ADC)$, in which Si is the signal intensity (SI) measured on the $_i$th b value image, bi is the corresponding b value, and $S_0$ is a variable estimating the intrinsic SI (for b=0 seconds/mm$^2$).

For the calculation of different ADC values, tumors were freehand delineated only on the central slices with the largest cross-sectional areas on the original DWIs at the b value of 1000 s/mm$^2$, in order to avoid partial volume effects. The delineation of each tumor lesion was copied to all images with different b values automatically. The average SI per tumor and per b value was then determined. The difference between $ADC_{low}$ (b=0, 50 and 100 s/mm$^2$) and $ADC_{high}$ (b=600, 800 and 1000 s/mm$^2$) was defined as $ADC_{perf}$ to reflect the tissue microcapillary perfusion, while $ADC_{high}$ was defined as $ADC_{diff}$ [Chen et al. (2007) *Methods*. 43, 12-20].

Digital Microangiography

After the last MRI scanning, rats were anesthetized by an intraperitoneal injection of pentobarbital at 50 mg/kg. Then laparotomy was performed with blood collected via postcava and abdominal aorta cannulated, through which barium suspension was injected before the entire tumor-bearing liver was excised. With a digital mammography unit (Embrace; Agfa-Gevaert, Mortsel, Belgium), postmortem hepatic arteriography was made at 26 kV, 32 mAs to document changes in tumor vascularity. The livers were then fixed and sliced into 3-mm sections in the axial plane corresponding to the MR images, and these sections were radiographed at 26 kV, 18 mAs for qualitative analysis.

Histopathology

After microangiography, the tumor sections were paraffin imbedded, sliced into 5 μm thickness and stained with hematoxylin and eosin (H&E) for microscopic analysis using an Axiovert 200M microscope equipped with an AxioCam MR monochrome digital camera (Carl Zeiss Inc, Gottingen, Germany) and by AxioVision 4.8 software.

Diagnosis of HCCs

Due to the high analogy to the histopathological progression observed in human liver cancer, rat primary HCCs were diagnosed according to the classical histomorphologic features: malignant hepatocytic tumors, often well vascularized, with wide trabeculae (>3 cell layers), noticeable acinar pattern, small cell changes, cytologic atypia, prominent nucleoli, mitotic activity, vascular invasion, absence of Kupffer cells and the loss of the reticulin network. The differentiation of rat HCCs was further classified into Grade I-IV using a modified 4-scale Edmondson and Steiner system [Schlageter et al. cited above].

2) Calculation of CA4P-Induced Intratumoral Necrosis

Digital images of tumor slices at a magnification of 12.5 were used to estimate the percentage of tumor necrosis by ImageJ software [Buijs et al. (2011) *J Vasc Interv Radiol* 22, 1175-1180]. Briefly, regions of interest were delineated around the entire tumor and the necrotic tumor, respectively, to get 'necrotic ratio on each section'. For each tumor section, the axial slide representing this tumor block was selected as 'section area'. Tumor necrosis on each H&E stained slice was estimated independently by 2 pathologists, and calculated with the equation: Intratumoral necrosis ratio (%)=Σ[Necrotic ratio on each section (%)×section area (mm$^2$)]×section thickness (mm)/[4/3π r$^3$] (mm$^3$).

Statistical Analysis

Statistical analyses were carried out by GraphPad Prism (version 7.02, GraphPad Software Inc, La Jolla, Calif., USA). The Pearson's correlation coefficient was calculated between percentile tumoral necrosis calculated by histopathology and tumor diameter measured from T2WI. Numerical data were presented as mean±standard errors of the mean (SEM). Comparison of percentile tumoral necrosis was performed by unpaired two-way t-test; results of ADCs between tumor and liver background were compared by two-way ANOVA. A significant difference was concluded for P<0.05.

The invention claimed is:

1. A method of treating an avascular tumor or hypovascular tumor with a diameter less than 20 mm comprising the step of administering an effective amount of a vascular disrupting agent (VDA) or salt or solvate or prodrug thereof, wherein the VDA is a combretastatin, and wherein the avascular tumor is not metastatic or the hypovascular tumor is not metastatic.

2. The method according to claim 1, which is combined or followed by an effective adjunct therapy.

3. The method according to claim 2, wherein the adjunct therapy is an intravascular administration of a further therapeutic agent one day after the administration of the VDA agent.

4. The method according to claim 3, wherein the further therapeutic agent is a radiotherapeutic agent targeting necrotic tissue.

5. The method according to claim 4 wherein the further therapeutic agent is iodine-131 labeled hypericin.

6. The method according to any one of claims 1 to 5, wherein the tumor has a diameter below 10 mm.

7. The method according to claim 1, wherein the tumor is a human tumor.

8. The method according to claim 7, wherein the administering is an intravenous administration.

9. The method according to claim 1, wherein the VDA is selected from the group consisting of CA4P, Oxi4503, AVE8062, MN-029, ZD6126, NP1-2358, and CYT997.

* * * * *